US00PP28564P2

(12) United States Plant Patent
Ui et al.

(10) Patent No.: US PP28,564 P2
(45) Date of Patent: Oct. 24, 2017

(54) ***PETUNIA* PLANT NAMED 'SAKPET098'**

(50) Latin Name: *Petunia hybrida*
Varietal Denomination: SAKPET098

(71) Applicant: Sakata Seed Corporation, Yokohama (JP)

(72) Inventors: Akinobu Ui, Iwata (JP); Randy Holbert, Salinas, CA (US)

(73) Assignee: Sakata Seed Corporation, Yokohama (JP)

( * ) Notice: Subject to any disclaimer, the term of this patent is extended or adjusted under 35 U.S.C. 154(b) by 0 days.

(21) Appl. No.: 14/999,105

(22) Filed: Mar. 30, 2016

(51) Int. Cl.
*A01H 5/02* (2006.01)

(52) U.S. Cl.
USPC ..... Plt./356.1

(58) Field of Classification Search
USPC ..... Plt./356.1
See application file for complete search history.

*Primary Examiner* — Annette Para
(74) *Attorney, Agent, or Firm* — Barbara Campbell; Bethany R. Roahrig; Cochran Freund & Young, LLC

(57) ABSTRACT

A *petunia* plant particularly distinguished by having a reddish-purple and white star-patterned flower color and green leaves, is disclosed.

2 Drawing Sheets

Genus and species: *Petunia hybrida.*
Variety denomination: 'SAKPET098'.

BACKGROUND OF THE NEW PLANT

The present invention comprises a new and distinct variety of *petunia* plant, botanically known as *Petunia hybrida*, and referred to by the variety name 'SAKPET098'. *Petunia* variety 'SAKPET098' originated from a hybridization in Kakegawa, Japan in June 2010. The female parent was a proprietary *petunia* line named '9BCR-49a' (unpatented), and the male parent was a proprietary *petunia* line named '9BCR-27-V2'.

In June 2010, '9BCR-49a' and '9BCR-27-V2' were crossed and 5,000 seeds were obtained. In February 2011, 50 F1 seeds were sown in the greenhouse and 30 plants were cultivated which produced flower colors of violet and white star-pattern, and blue and magenta with mounding and semi-mounding plant habits. In June 2011, 3 plants were selected which had violet star-patterned bi-colored flowers and a semi-mounding plant habit. In July 2011, about 15,000 seeds of the flowers were sown in the greenhouse and 120 plants were cultivated which produced flowers of violet star-patterned bi-colored flowers, rose star-patterned bi-colored flowers, light-magenta and magenta with mounding and semi-mounding plant habits. In March 2013, a single plant line was selected within the F2 and named 'L2013-041'. 'L2013-041' was vegetatively propagated, cultivated, and transplanted to the field for evaluation outdoors. In January 2014, 'L2013-041' was vegetatively propagated, cultivated, and evaluated again. The breeder confirmed that 'L2013-041' was fixed and stable for traits. From February through March 2015, 'L2013-041' was evaluated for day-length neutral flowering response. 'L2013-041' was subsequently named 'SAKPET098'. 'SAKPET098' was found to reproduce true to type in successive generations of asexual propagation via vegetative cuttings in Salinas, Calif.

SUMMARY

The following are the most outstanding and distinguishing characteristics of this new variety when grown under normal horticultural practices in Salinas, Calif.

1. Reddish-purple and white star-patterned flowers; and
2. Green leaves.

DESCRIPTION OF THE PHOTOGRAPHS

This *Petunia* plant is illustrated by the accompanying photographs which show the plant's overall plant habit including form, foliage, and flowers. The photographs are of a plant grown in Salinas, Calif. under greenhouse conditions. The colors shown are as true as can be reasonably obtained by conventional photographic procedures.

DESCRIPTION OF THE NEW VARIETY

Figure 1:
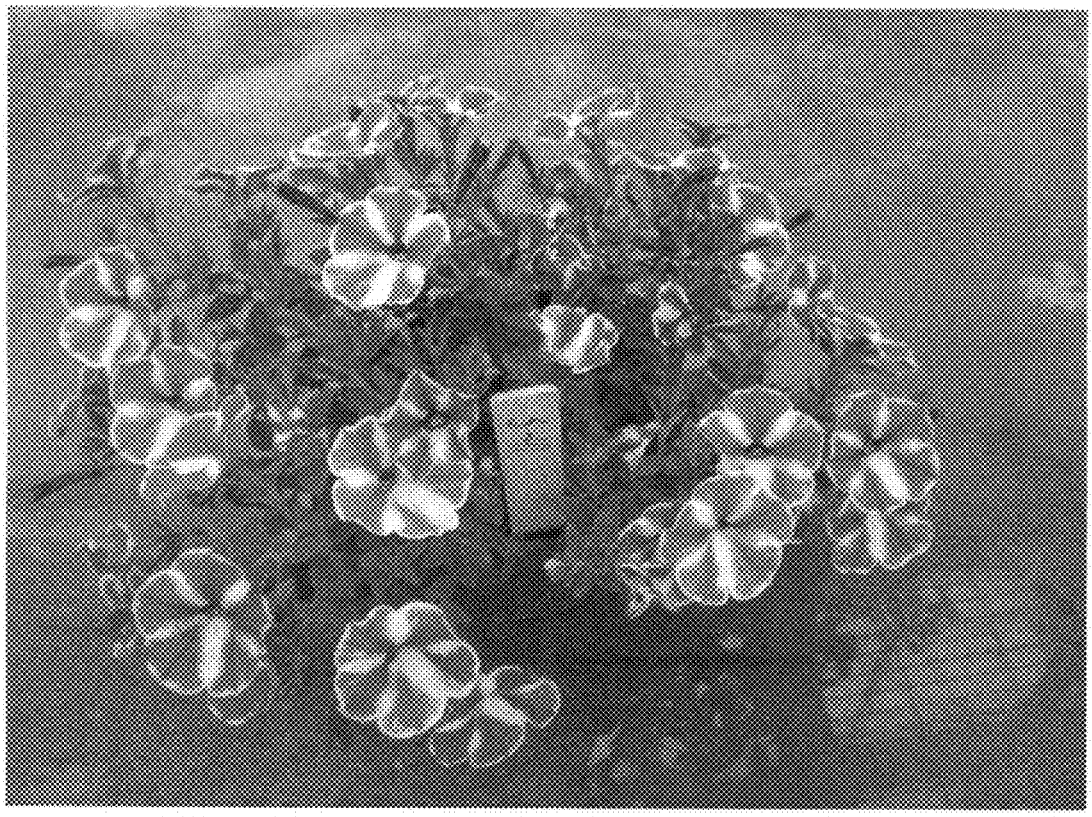
FIG. 1 shows the overall plant habit of the plant grown in a pot.
Figure 2:
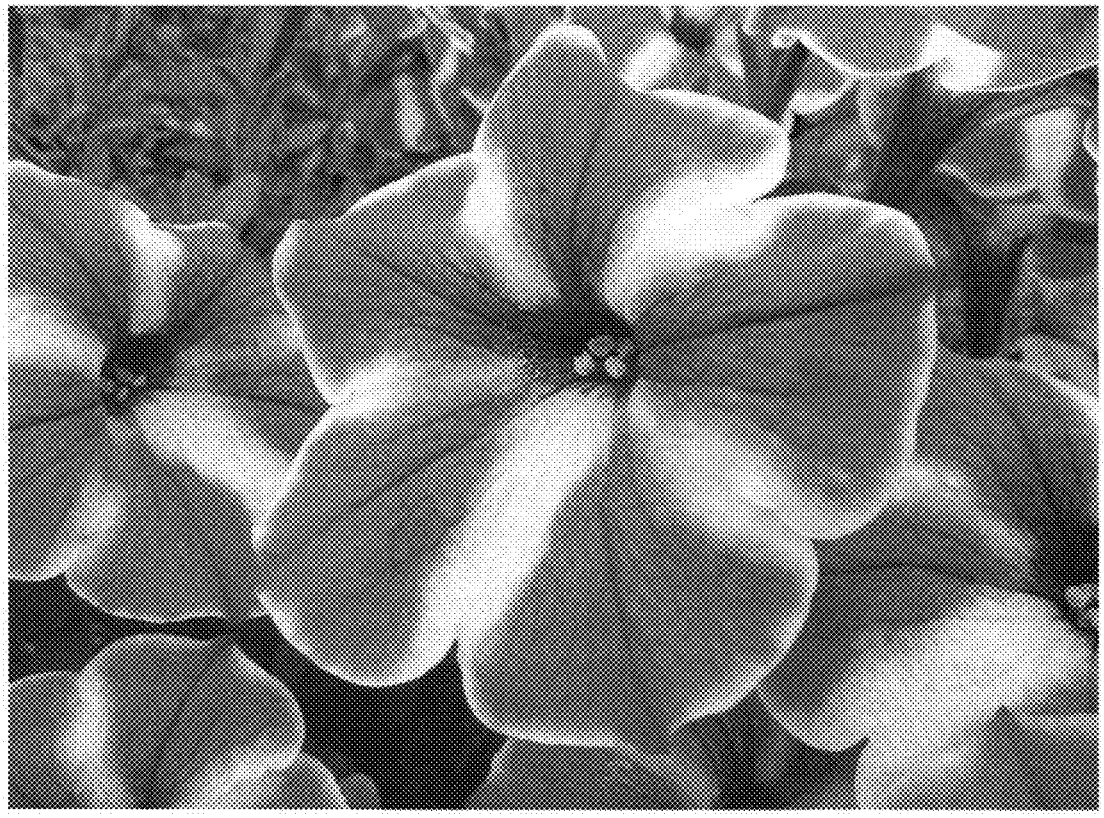
FIG. 2 shows a close-up of the mature inflorescence of the plant.

Data was obtained from plants grown six-months from transplant into 8-inch pots from rooted cuttings in Salinas, Calif. under greenhouse conditions. Plants were pinched once during growth. Color references are to The Royal Horticultural Society of London color chart (R.H.S.), 4$^{th}$ edition (2001). Anatomic labels are from *The Cambridge Illustrated Glossary of Botanical Terms*, by M. Hickey and C. King, Cambridge University Press.

Classification:

*Family.*—Solanaceae.
*Botanical.—Petunia hybrida.*
*Common.—Petunia.*
*Designation.*—'SAKPET098'.

Growth:

*Environmental conditions for plant growth.*—The terminal 1.0 to 1.5 inches of an actively growing stem was excised. The vegetative cuttings were propagated for five to six weeks. The base of the cuttings were dipped for 1 to 2 seconds in a 1:9 solution of DIP 'N GROW (1 solution:9 water) root inducing solution immediately prior to sticking into the cell trays. Cuttings were stuck into plastic cell trays having 98 cells, and containing a moistened peat moss-based growing medium. The cuttings were misted with water from overhead for 10 seconds every 30 minutes until sufficient roots were formed. Rooted cuttings were transplanted and grown in 20 cm diameter plastic pots in a glass greenhouse located in Salinas, Calif. Pots contained a peat moss-based growing medium. Soluble fertilizer containing 20% nitrogen, 10% phosphorus and 20% potassium was applied once a day or every other day by overhead irrigation. Pots were top-dressed with a dry, slow release fertilizer containing 20% nitrogen, 10% phosphorus and 18% potassium. The typical average air temperature was 24° C.

Parentage:

*Female parent*.—The proprietary *petunia* line '9BCR-49a' (unpatented).

*Male parent*.—The proprietary *petunia* line '9BCR-27-V2'.

Plant description:

*Habit*.—Mounding and semi-trailing.

*Height*.—About 22.5 cm from the soil line to the top of the foliage.

*Spread*.—About 44.0 cm.

*Number of branches per plant*.—About 10 main basal branches; many secondary and tertiary branches.

*Length of branches*.—17.0 cm to 20.0 cm.

*Diameter of branches*.—3.0 mm.

*Life cycle*.—Annual; tender perennial in some climates.

*Time to produce a rooted cutting*.—About 4 weeks.

*Time to bloom from propagation*.—6 to 8 weeks.

*Flowering requirements*.—Will flower so long as the temperature is above 13° C. and greater than 12 hours of daylight.

*Temperature tolerances*.—No particular temperature tolerances observed.

Stems:

*Color*.—Closest to RHS 143A (Green).

*Anthocyanin*.—Absent.

*Pubescence*.—Dense (heavy).

*Pubescence color*.—RHS N155A (White).

*Description and appearance*.—Pliable; circular in cross-section.

*Length*.—About 13.5 cm.

*Diameter*.—2.0 mm.

*Internode length*.—About 1.5 cm.

Leaves:

*Arrangement*.—Alternate.

*Shape*.—Ovate.

*Apex*.—Obtuse.

*Base*.—Attenuate.

*Margin*.—Entire.

*Attachment*.—Sessile.

*Surface appearance* (*both surfaces*).—Dull, waxy, and sticky with slight to moderate pubescence.

*Length*.—2.5 cm.

*Width*.—1.3 cm.

*Color*.—Upper surface: RHS 137A (Green). Lower surface: Closest to RHS 147C (Yellow-green).

*Venation pattern*.—Pinnate.

*Venation color* (*both surfaces*).—RHS 144B (Yellow-green).

*Fragrance*.—Absent.

*Petiole*.—Absent.

Flowers:

*Number of flowers in bloom*.—90 to 100.

*Number of flowers per node*.—1.

*Inflorescence type*.—Single.

*Fragrance*.—Absent.

*Flower depth*.—About 3.5 cm.

*Flower diameter*.—5.8 cm.

Corolla:

*Shape*.—Funnel-shaped with five fused petals.

*Diameter*.—5.8 cm.

*Depth*.—6.0 mm.

*Petals*.—Surface texture (both surfaces): Glabrous. Length: 2.8 cm. Width: 3.0 cm. Shape: Obcordate. Apex: Abruptly acute. Margin: Entire. Color: Upper surface: Closest to RHS N78A (Purple) and RHS N155C (White) with RHS N79A (Purple) at the mid-vein. Lower surface: Closest to RHS 77A (Purple) and RHS N155C (White).

*Corolla tube*.—Tube length: 2.5 cm. Tube diameter: 1.0 cm. Tube pubescence (both surfaces): Dense pubescence. Tube pubescence color: RHS N155A (White). Color, inner surface: RHS 79A (Purple) with RHS N155C (White) and a slight RHS 145A (Yellow-green). Color, outer surface: Closest to but darker than RHS 79B (Purple) with RHS 79A (Purple) veins on most, some alternate colors with RHS 79A (Purple) and RHS 145C (Yellow-green) with RHS 145A (Yellow-green) veins.

Calyx:

*Form*.—Composed of 5 sepals.

*Attachment*.—Sessile.

*Apex*.—Obtuse.

*Base*.—Attenuate.

*Margin*.—Entire.

*Length*.—1.6 cm.

*Width*.—3.0 mm.

*Color*.—Upper surface: Closest to RHS 138A (Green). Lower surface: Closest to RHS 144A (Yellow-green).

Bud:

*Surface texture and appearance*.—Dull, sticky, with heavy pubescence; pubescence color is RHS N155A (White).

*Length*.—3.8 cm.

*Diameter*.—6.0 mm.

*Shape*.—Cylindrical.

*Color*.—RHS N92A (Violet-blue) at the center; RHS N187A (Greyed-purple) at the tip; slight RHS 144D and RHS 157A at the tip.

Peduncle:

*Length*.—1.7 cm to 2.3 cm.

*Diameter*.—1.5 mm.

*Color*.—RHS 143C (Yellow-green) with heavy pubescence; pubescence color is RHS N155A (White) with very slight RHS N187A (Greyed-purple) towards the flower bud.

Reproductive organs:

*Stamens*.—Form: Arranged adjacent to the pistil. Number: 5, free. Length: 2.5 cm to 2.8 cm. Filament color: RHS 145D (Yellow-green) with RHS 155C (White). Anther color: RHS 279C (Grey). Pollen color: RHS 97B (Violet-blue). Pollen description: Powdery; abundant.

*Pistil*.—Number: 1. Length: 2.5 cm. Stigma color: RHS 79C (Purple). Stigma length: 2.0 mm. Style color: RHS 145D (Yellow-green). Style length: 2.3 cm. Ovary arrangement: Superior. Ovary surface color: RHS 143C (Green).

*Seed production*.—Not observed.

Disease and insect resistance: No particular resistance or susceptibility observed.

COMPARISON WITH PARENTAL LINES AND SIMILAR VARIETY

'SAKPET098' can be compared with the parental lines, as shown in Table 1.

TABLE 1

| Characteristic | 'SAKPET098' | Female Parent '9BCR-49a' | Male Parent '9BCR-27-V2' |
|---|---|---|---|
| Flower color | Reddish-purple and white star-patterned flowers | Blue and white star-patterned bi-colored flowers | Red |
| Plant growth habit | Mounding and semi-trailing | Semi-mounding | Mounding |

'SAKPET098' can be compared with the similar commercial variety 'SAKPET096' (U.S. Plant Pat. No. 27,309) as shown in Table 2.

TABLE 2

| Characteristic | 'SAKPET098' | 'SAKPET096' |
|---|---|---|
| Petal color, upper surface | Closest to RHS N78A (Purple) and RHS N155C (White) with RHS N79A (Purple) at mid-vein | RHS N74A (Red-Purple), RHS N74B (Red-Purple) and RHS N155A (White) with RHS 77A (Purple) at the mid-vein |
| Petal color, lower surface | Closest to RHS 77A (Purple) and RHS N155C (White) | RHS N74C (Red-Purple) with RHS N77A (Purple) at the mid-vein |
| Flower diameter | 5.8 cm | 4.5 cm |
| Plant habit | Mounding and semi-trailing | Mounding |

We claim:

1. A new and distinct variety of *petunia* plant named 'SAKPET098' as described and illustrated herein.

* * * * *